US00PP12408P2

(12) United States Plant Patent
Utecht

(10) Patent No.: US PP12,408 P2
(45) Date of Patent: Feb. 12, 2002

(54) GERANIUM PLANT NAMED 'FISBEACH'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/631,662

(22) Filed: Aug. 3, 2000

(51) Int. Cl.[7] ..... A01H 5/00
(52) U.S. Cl. ..... Plt./332
(58) Field of Search ..... Plt./332, 324

(56) References Cited

PUBLICATIONS

Fischer Selections 1999/2000 Catalogue offering Beach 99 ('Fisbeach').
Swiss Application for 'Fisbeach' (Apr. 22, 1999).
European Union Application for 'Fisbeach' (Aug. 17, 1998).
European Union Grant for 'Fisbeach' (Aug. 16, 1998).
German Application for 'Fisbeach' (Aug. 15, 1997).
German Denomination for 'Fisbeach' (Jul. 15, 1998).
German Grant for 'Fisbeach' (Jan. 15, 1999).
GTITM UPOVROM Citation for 'Fisbeach' as per QZ PBR 9809830; Jun. 15, 1998.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisbeach', as described and illustrated, and particularly characterized by the combined features of brilliant-red, double flowers, compact inflorescence borne well-above the foliage, fresh-green, slightly crenated foliage without zonation, vigorous growth and well-branched, bushy and uniform plant habit.

1 Drawing Sheet

BACKGROUND OF THE INVENTION

The present invention relates to a new and distinct cultivar of geranium plant, botanically known as *Pelargonium peltatum*, and hereinafter referred to by the cultivar name 'Fisbeach'.

'Fisbeach' is a product of a planned breeding program which had the objective of creating new geranium cultivars with red-flower color, vigorous growth, and bushy and well-branched plant habit.

'Fisbeach' originated from a hybridization made by the inventor, Angelika Utecht, in a controlled breeding program in Galdar, Gran Canaria, Spain, in 1992. The female parent was a hybrid seedling, designated No. 361-7 (unpatented), characterized by dark-red, double flowers, medium-green, slightly zoned foliage, and vigorous growth but poorly-branched habit. The male parent was the cultivar 'Guimo' (unpatented), commercially known as 'Momo', characterized by scarlet, single-type flowers, large foliage without zonation, good branching ability and relatively vigorous growth. The zonation on the young leaves of 'Fisbeach' is very weak.

'Fisbeach' was selected as one flowering plant within the progeny of the stated cross by the inventor, Angelika Utecht, in 1993 in a controlled environment in Galdar, Gran Canaria, Spain.

The first act of asexual reproduction of 'Fisbeach' was accomplished when vegetative cuttings were taken from the initial selection in autumn 1993 in a controlled environment in Galdar, Gran Canaria, Spain, by, or under the supervision of, Angelika Utecht. Horticultural examination of plants grown from these cuttings, initiated in May 1996, in Hillscheid, Germany, and continuing thereafter, has demonstrated that the combination of characteristics as herein disclosed for 'Fisbeach' are firmly fixed and are retained through successive generations of asexual reproduction.

BRIEF DESCRIPTION OF THE INVENTION

The following traits have been repeatedly observed and are determined to be basic characteristics of 'Fisbeach', which in combination distinguish this geranium as a new and distinct cultivar:

1. Brilliant-red, double flowers;
2. Compact, semi-spherically shaped inflorescences;
3. Uniform-green foliage without zonation;
4. Vigorous growth in combination with good branching characteristics; and
5. Early to medium spring flowering response.

'Fisbeach' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisbeach' is the related variety 'Fisbea' (U.S. Plant Pat. No. 10,851). In comparison to 'Fisbea', 'Fisbeach' has better branching characteristics and develops a dense, bushy, uniformly round plant habit with the inflorescences borne higher above the foliage. Furthermore, 'Fisbeach', in contrast to 'Fisbea', shows almost no infusion of anthocyanin on pedicels, sepals or peduncles under outdoor conditions, and the red flower color is more stable and hardly tends to fade. Additionally, the leaves of 'Fisbeach' are more distinctly crenated at the margin and show slightly stronger waving and lobing of the margin than the leaves of 'Fisbea'.

BRIEF DESCRIPTION OF THE DRAWINGS

The accompanying photographic illustration shows typical flower and foliage characteristics of 'Fisbeach' with colors being as true as possible with an illustration of this type.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium peltatum* L'Hérit.

*Commercial.*—Ivy geranium, cv. 'Fisbeach'.

Inflorescence:

*Umbel.*—Shape: Semi-spherical. Average diameter: 77 mm. Average depth: 40 mm. Peduncle length: 143 mm. Peduncle color: Light to medium-green, RHS 143 B. Pedicel length: 21 mm. Pedicel color: Green RHS 144 A, no infusion of anthocyanin. Number of flowers per umbel: About 10–12. Lastingness of umbel: Approximately 14–15 days.

*Corolla.*—Average diameter: 48 mm. Form: Double. Shape: Outline round, many narrow petals, which are not always overlapping, open middle. Number of petals: 18.4. Size of petals: Upper petals 29–31 mm long, 15–17 mm wide; lower petals 25–27 mm long, 15–17 mm wide. Shape of petals: Upper petals are spatulate, lower petals are obovate, attenuate base, upper end rounded, margin mainly entire but slightly crenated or denated at the tip. Number of petaloids: 0–2. Color of petaloids: Upper and lower surface RHS 46 C, with white RHS 155 D to pale pink RHS 56 A at the base. Color (general tonality from a distance of three meters): Brilliant-red. Color of upper petals: RHS 45 A. Markings of upper petals: Two weak, blackish veins RHS 187 A, which are dark-violet RHS 187 D on the lower surface. Color of lower petals: RHS 45 B. Color of lower surface of petals: RHS 46 C. Color of sepals: Outer surface light green RHS 143 B indoors, reddish RHS 179 A outdoors; inner surface light green RHS 143 B indoors, outdoors RHS 179 B, no infusion of anthocyanin indoors. Number of sepals: 5.

*Bud* (*just before petals unfold*).—Shape: Elliptical. Color (sepals): Green, RHS 143 A. Color (petals): Red, RHS 46 B. Length: 14 mm. Width: 9 mm. Size of sepals: 15–16 mm long, 4–5 mm wide for the largest upper sepal, 2–3 mm in width for the other sepals. Shape of sepals: Linear to lanceolate, acute tip, base truncate, very weak pubescence, margin entire.

*Reproductive organs.*—Androecium: 5–7 fertile anthers with white to pink filaments and yellow-orange pollen RHS 30 A, moderate quantity of pollen produced. Gynoecium: 5–6 lobed, dark-red-colored stigma RHS 46 A, whitish filament with color varying between RHS 155 D to RHS 56 A, one pistil per flower. Fertility/seed set: No seed set observed.

*Spring flowering response period.*—In Hillscheid, Germany, in 1999, plants had on average 1.0 flowers opened 12 weeks after planting of unrooted cuttings.

*Outdoor flower production.*—Medium to rich flowering, the flower count in 1999, in Hillscheid, Germany, indicated about 4.25 inflorescences per plant in mid-May.

*Durability.*—Good shatter resistance and relatively good rain resistance.

*Lastingness of individual bloom.*—Approximately 8 days at 18° C.

*Fragrance.*—None.

Plant:

*Foliage.*—Shape: Ivy-shaped with cordate, slightly open base and moderately lobed, slightly glossy surface. Margin: Partly entire, slightly crenated near the tips of the leaves. Texture: Slightly glassy surface. Size of leaf: 96 mm wide, 55 mm long. Color of upper surface: Green, varies between RHS 137 D and RHS 143 A. Color of lower surface: Light-green, RHS 143 B. Color of zonation: RHS 165 A weakly present on young leaves. Petiole size: 60–70 mm in length, 2–3 mm in diameter. Petiole color: Light green, RHS 143 C.

*General appearance and form.*—Internode length: 35–40 mm. Branching pattern: 14.8 branches. Size of plant/Length of branches: 24 cm (12 weeks after planting), 60–70 cm (in early September, 30 weeks after planting) as measured from the top of the soil to the tips of the branches.

Disease/pest resistance/susceptibility: None observed to date.

I claim:

1. A new and distinct cultivar of geranium plant named 'Fisbeach', as described and illustrated.

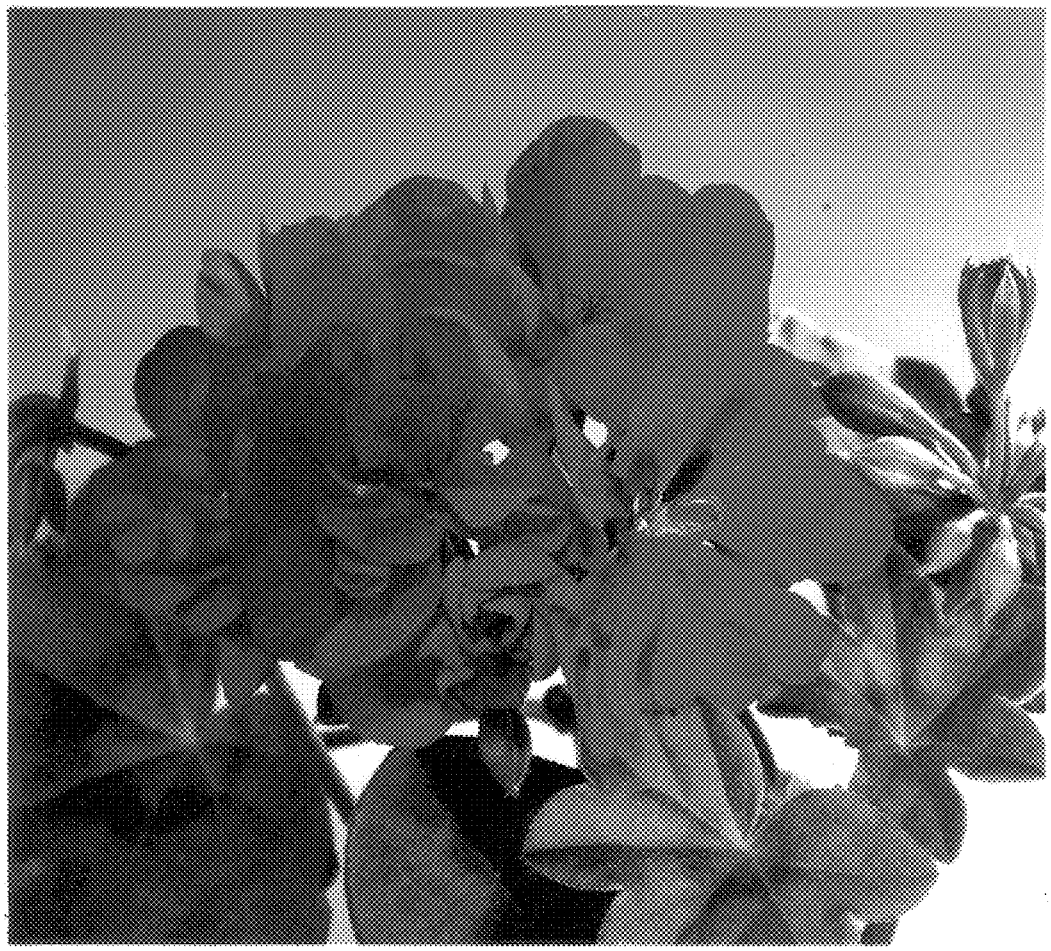

* * * * *